United States Patent
Plecko et al.

(10) Patent No.: US 9,486,261 B2
(45) Date of Patent: Nov. 8, 2016

(54) NAIL-PLATE COMBINATION

(75) Inventors: Michael Plecko, Graz (AT); Oliver Boesl, Rohr AG (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 742 days.

(21) Appl. No.: 12/677,995

(22) PCT Filed: Sep. 25, 2008

(86) PCT No.: PCT/US2008/077703
§ 371 (c)(1),
(2), (4) Date: Mar. 12, 2010

(87) PCT Pub. No.: WO2009/042783
PCT Pub. Date: Apr. 2, 2009

(65) Prior Publication Data
US 2010/0256685 A1    Oct. 7, 2010

Related U.S. Application Data

(60) Provisional application No. 60/975,729, filed on Sep. 27, 2007, provisional application No. 60/981,843, filed on Oct. 23, 2007.

(51) Int. Cl.
*A61B 17/80* (2006.01)
*A61B 17/72* (2006.01)

(52) U.S. Cl.
CPC ......... *A61B 17/8061* (2013.01); *A61B 17/725* (2013.01); *A61B 17/8014* (2013.01); *A61B 17/8057* (2013.01)

(58) Field of Classification Search
CPC .................................... A61B 17/8061
USPC .................................. 606/64–67, 289, 295
See application file for complete search history.

(56) References Cited

U.S. PATENT DOCUMENTS

| | | | |
|---|---|---|---|
| 5,300,074 A | 4/1994 | Frigg | |
| 7,771,457 B2* | 8/2010 | Kay et al. | 606/284 |
| 8,157,803 B1* | 4/2012 | Zirkle, Jr. | A61B 17/744 606/64 |
| 2003/0135212 A1 | 7/2003 | Chow | |
| 2006/0100623 A1* | 5/2006 | Pennig | 606/64 |
| 2006/0200145 A1 | 9/2006 | Kay et al. | |

FOREIGN PATENT DOCUMENTS

| | | |
|---|---|---|
| CN | 2922820 | 7/2007 |
| EP | 0 689 800 | 1/1996 |
| EP | 1 398 000 | 3/2004 |
| WO | 2005/096977 | 10/2005 |

\* cited by examiner

*Primary Examiner* — Andrew Yang
(74) *Attorney, Agent, or Firm* — Kay Kaplun & Marcin, LLP

(57) ABSTRACT

A device for treating a bone includes a plate having a connector opening and a first fastener receiving lumen extending therethrough, the first fastener receiving lumen being sized and shaped to receive therethrough a bone fastener and a nail sized and shaped for insertion in a medullary canal of a target bone, the nail including an elongate shaft and an opening extending through the shaft in combination with a connector sized and shaped so that, when the plate is positioned over a target portion of bone in a desired alignment with the nail, the connector may be passed into the target portion of bone via the connector opening and into the opening of the nail, the shape of the connector engaging the opening to form an angularly stable connection between the plate and the nail.

21 Claims, 21 Drawing Sheets

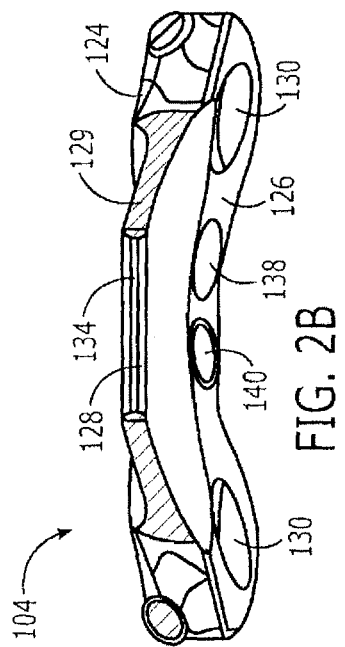
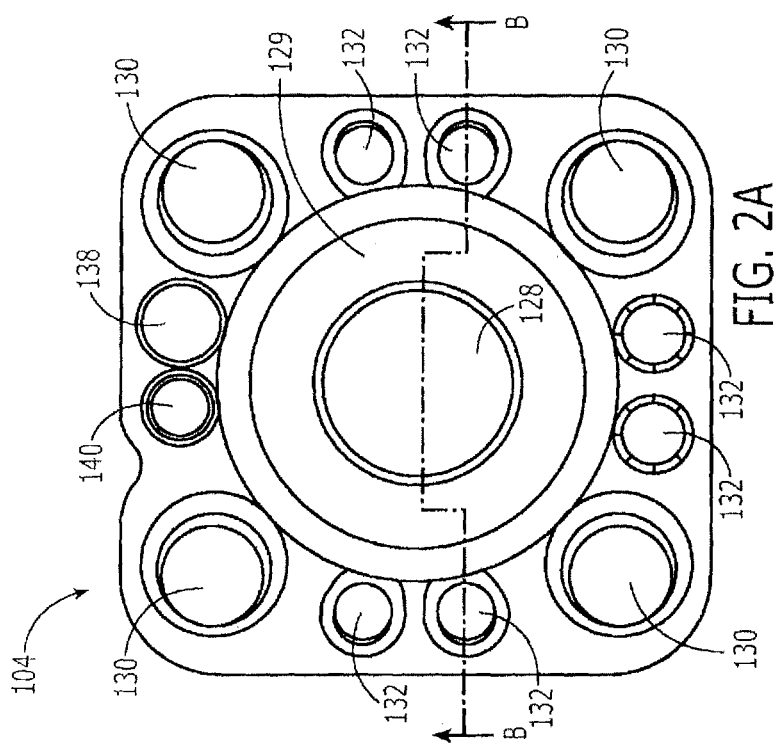

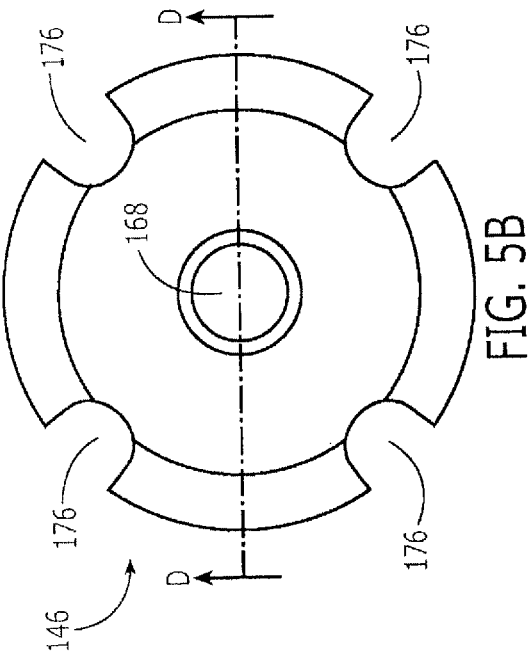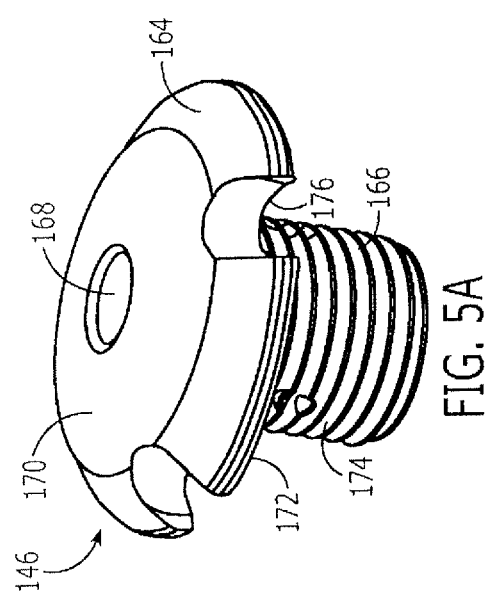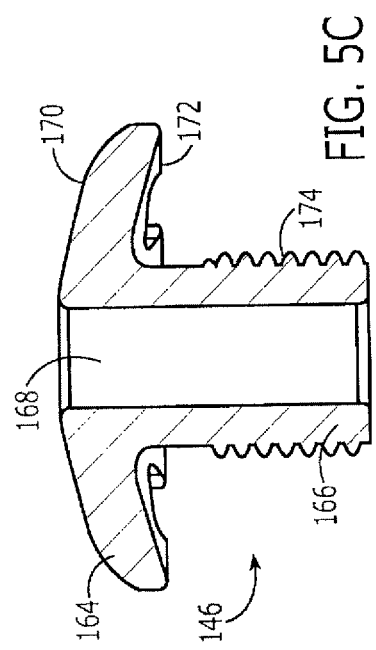

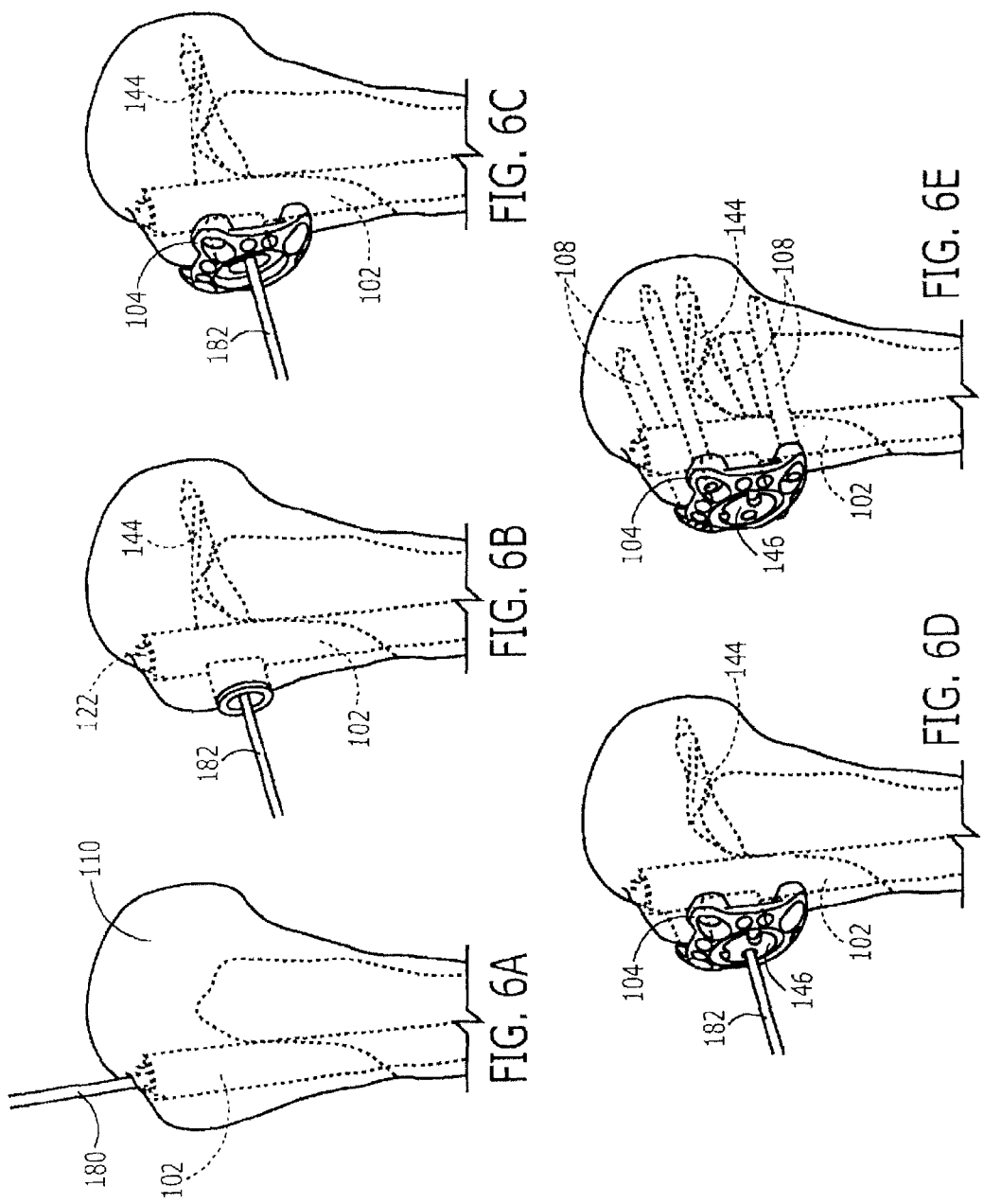

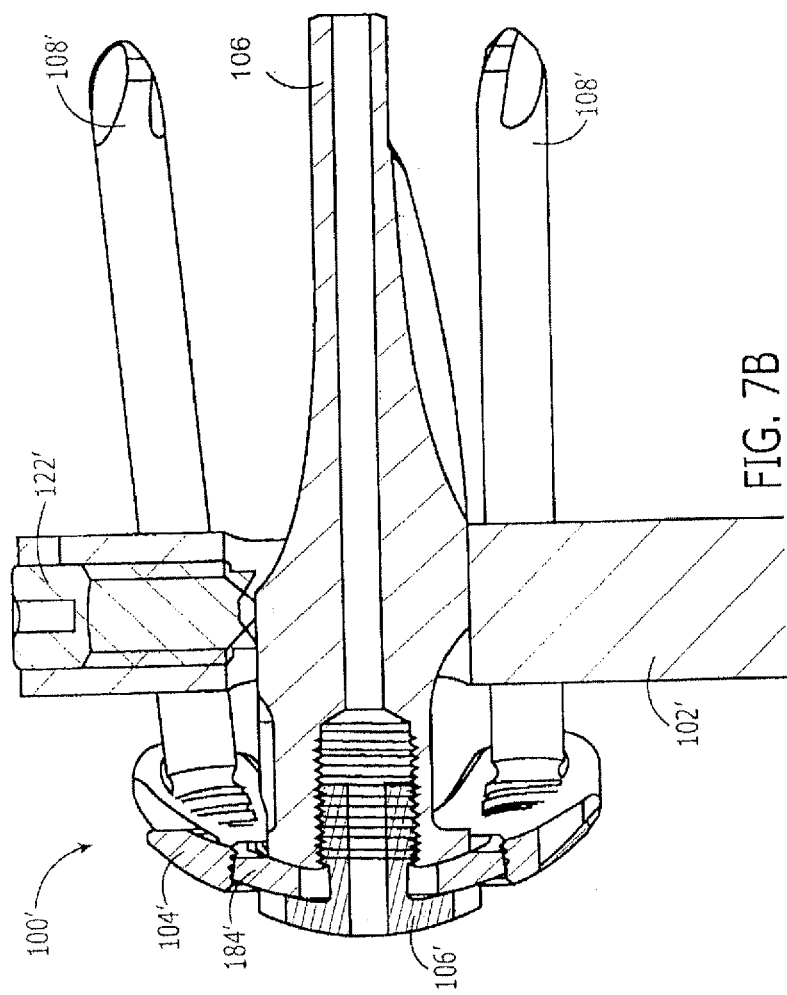
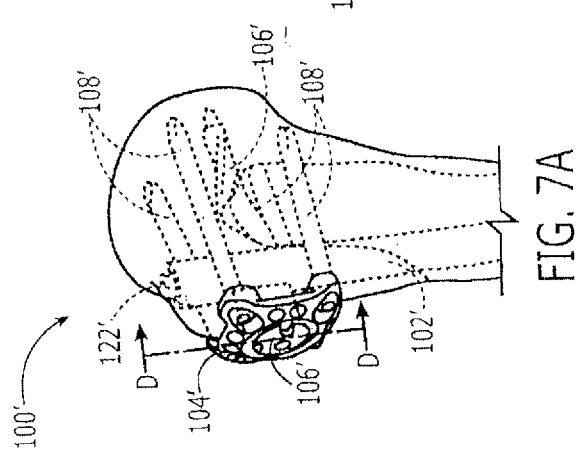

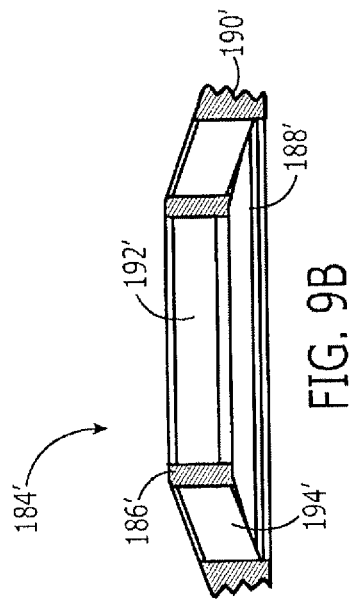
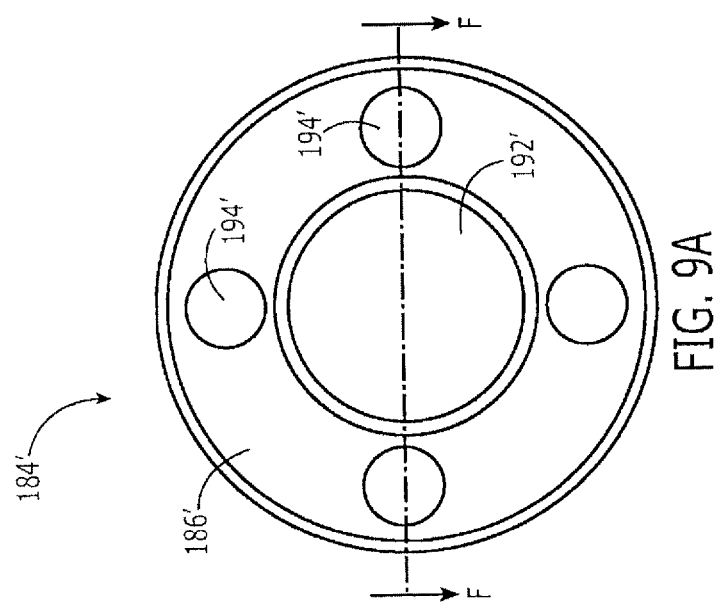
FIG. 9B
FIG. 9A

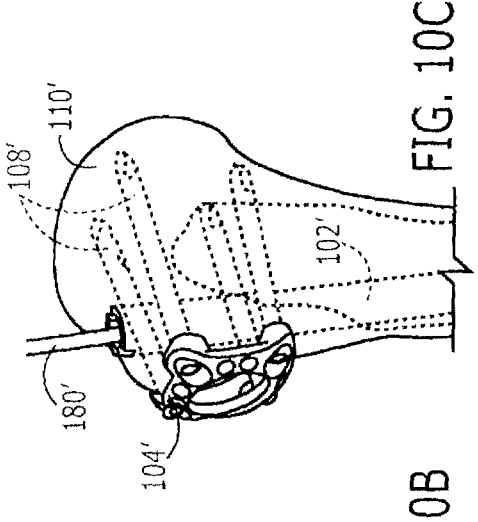
FIG. 10A
FIG. 10B
FIG. 10C
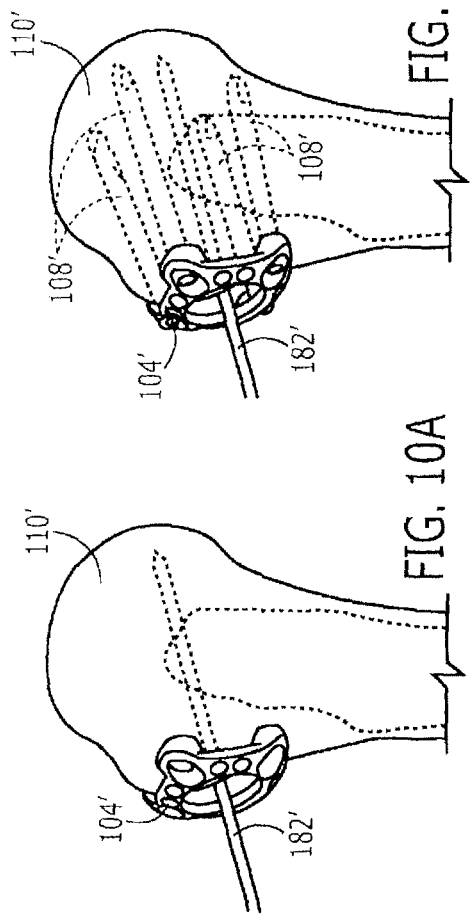
FIG. 10D
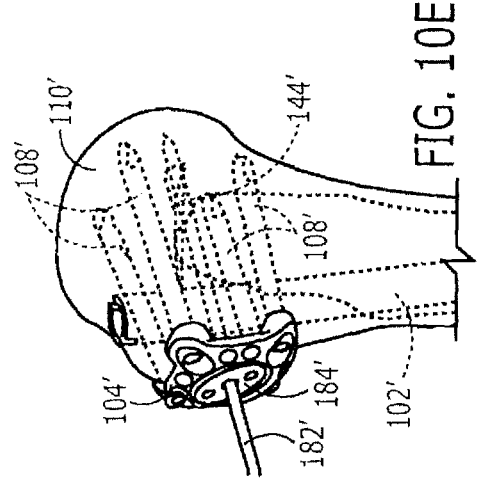
FIG. 10E
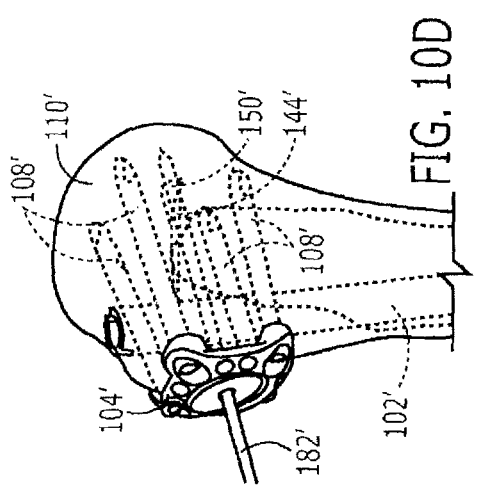
FIG. 10F

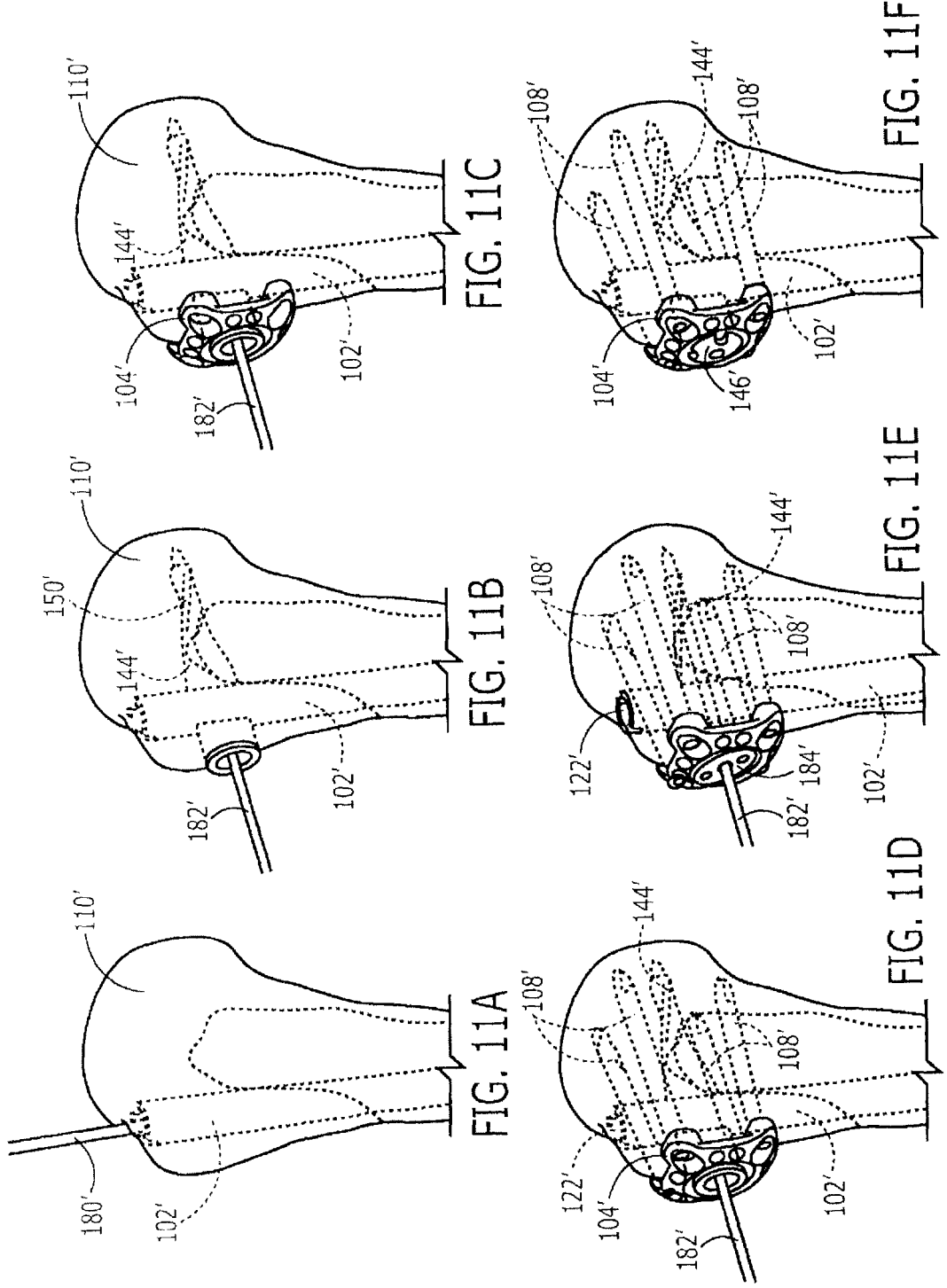

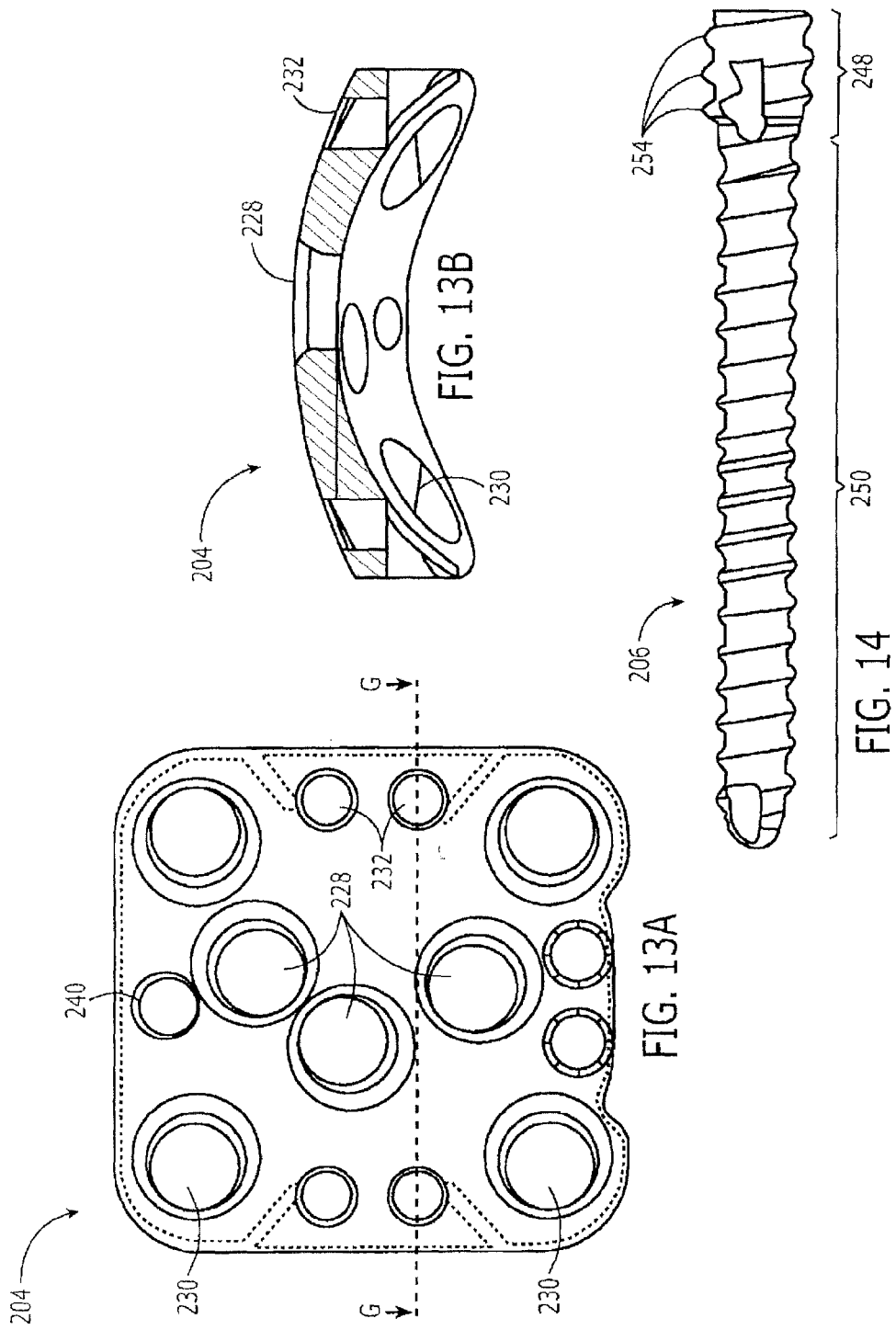

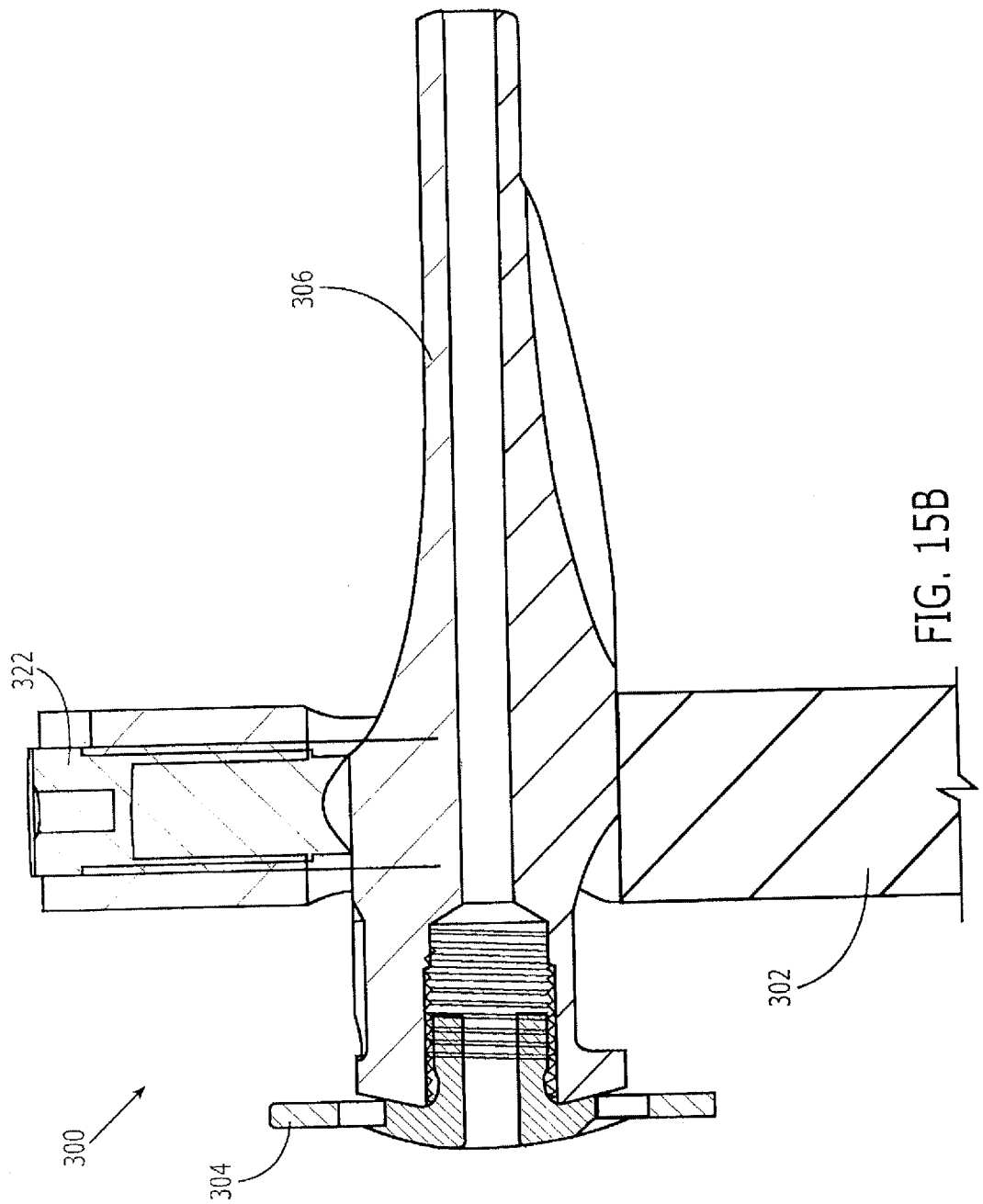

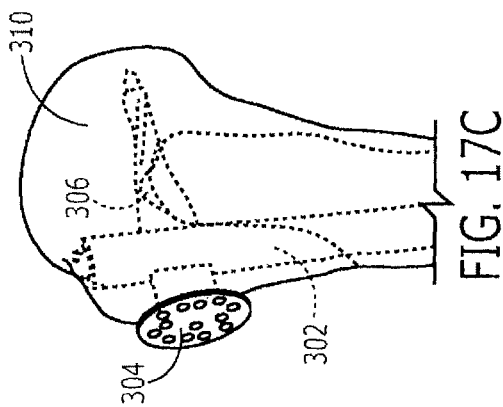
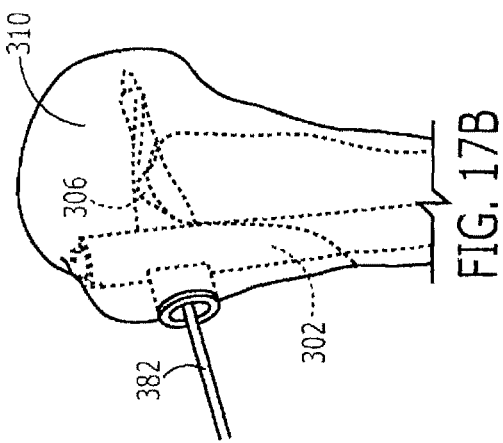
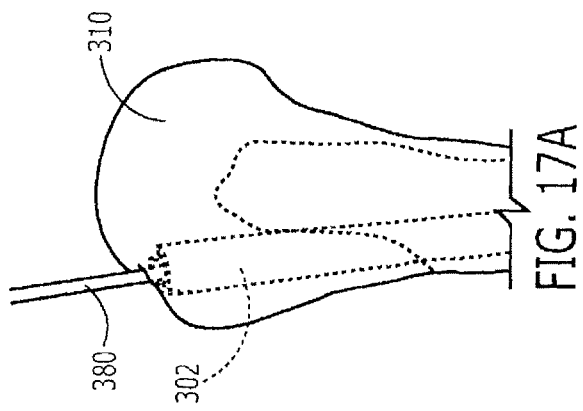

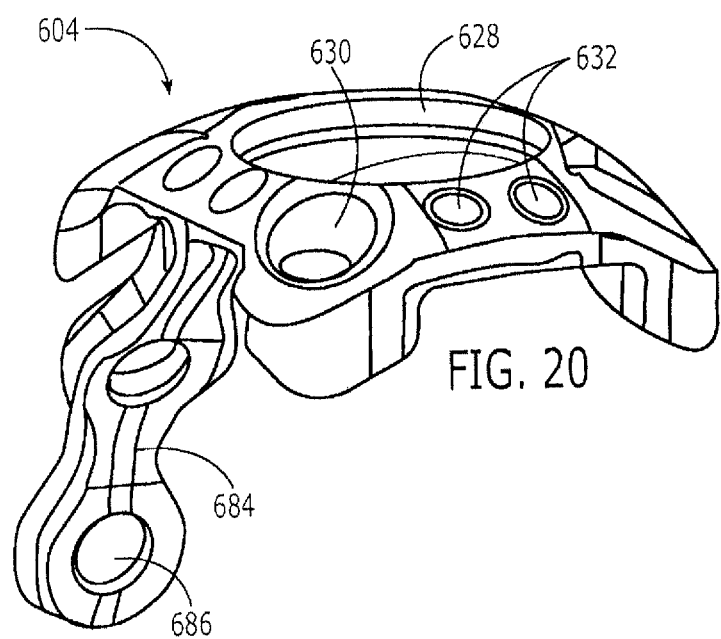

NAIL-PLATE COMBINATION

CROSS-REFERENCE TO RELATED APPLICATIONS

The subject matter disclosed in this patent application is related to subject matter disclosed and claimed in U.S. Provisional Patent Application No. 60/975,729 filed Sep. 27, 2007 and U.S. Provisional Patent Application No. 60/981,843 filed Oct. 23, 2007 both of which are incorporated herein by reference in their entireties.

FIELD OF THE INVENTION

The invention relates generally to implants for bone fixation and, in particular, to implants for fixation of multi-part fractures and two-part fractures with poor bone purchase (osteoporosis) of the proximal humerus to promote osteosynthesis.

BACKGROUND

As understood by those skilled in the art, proximal humeral fractures (fractures of the head or cortex) often result from a fall on the humerus. In a two-part fracture, the head or a single portion of the head is broken from the humeral shaft. Multi-part fractures involve the fracture of the humeral head into two or three fragments that separate from the shaft. Poor bone purchase is often a result of osteoporosis.

Conventional treatment of multi-part humeral fractures often involves wiring, suturing, or externally fixing the fragments to one another and/or to the humeral shaft. For example, a nail may be inserted into the medullary canal of the humerus and one or more screws may be inserted into the head of the humerus and fixed to the nail. According to another example, fractured fragments of a humeral head may be secured together by an elongated plate that is secured to the shaft of the humerus.

Post-operative complications may arise when the patient applies a load to the healing bone. For example, a screw may be forced out of the humeral head or a plate may bend or break.

SUMMARY OF THE INVENTION

This Summary is provided to introduce a selection of concepts in a simplified form that are further described below in the Detailed Description of Illustrative Embodiments. This Summary is not intended to identify key features or essential features of the invention, nor is it intended to limit the scope of the invention.

The invention provides a plate that secures together fragments of a fractured head of a bone with fasteners. Additionally, the plate securing the fractured bone is connected to a nail in the medullary canal of the bone using an angularly stable connector, which may be a spiral blade, a screw or any other stable connector. According to one embodiment, the angularly stable connector is a spiral blade inserted through an opening in the plate and into an oblong opening in the nail. According to another embodiment, the angularly stable connector includes a plurality of screw connectors, each of which is inserted through a connector opening in the plate and into an oblong opening in the nail.

Another aspect of the invention includes a method of treating complex fractures of the head of a bone. In one implementation, the fractured head of a bone is stabilized by securing bone fragments together with a plate and fasteners. Once the fractured head of the bone has been stabilized, an intramedullary nail is inserted into the medullary canal of the fractured bone and the plate is connected to the intramedullary nail using an angularly stable connector. The angularly stable connector is fixed to both the plate and the intramedullary nail to form a rigid connection. In another implementation, the intramedullary nail is first inserted into the medullary canal of the fractured bone and then the fractured head of the bone is stabilized by securing bone fragments together with a plate and fasteners. The plate is then connected to the intramedullary nail using an angularly stable connector. Again, the angularly stable connector is fixed to both the plate and the intramedullary nail to form a rigid connection.

The present invention is directed to a device for treating a bone, comprising a plate having a connector opening and a first fastener receiving lumen extending therethrough, the first fastener receiving lumen being sized and shaped to receive therethrough a bone fastener and a nail sized and shaped for insertion in a medullary canal of a target bone, the nail including an elongate shaft and a connector opening extending through the shaft transverse to a longitudinal axis of the shaft in combination with a connector sized and shaped so that, when the plate is positioned over a target portion of bone in a desired alignment with the nail, the connector may be passed into the target portion of bone via the connector opening and into the connector opening in the nail, the shape of the connector non-rotatably engaging the slot to form an angularly stable connection between the plate and the nail.

The present invention is further directed to a method of treating a bone, comprising the steps of securing to a target portion of a bone to be treated a plate including a connector opening and a fastener opening extending therethrough, inserting a fastener through the fastener opening and inserting into a medullary canal of the bone a nail including an elongate shaft and an opening of the nail extending through the shaft transverse to a longitudinal axis of the shaft in combination with the step of inserting a connector through the target portion of the bone via the connector opening and into the opening of the nail, at least a portion of the connector being shaped so that, when received within the slot, the connector is non-rotatable therein.

Additional features and advantages will be made apparent from the following detailed description of illustrative embodiments that proceeds with reference to the accompanying drawings.

BRIEF DESCRIPTION OF THE DRAWINGS

The foregoing summary, as well as the following detailed description may be better understood when read in conjunction with the appended drawings. For the purpose of illustrating the nail-plate combination and the method related thereto the drawings illustrate exemplary embodiments; however, the nail-plate combination and related methods are not limited to the specific embodiments and methods disclosed. Like reference numerals refer to corresponding parts throughout the several views of the drawings, wherein:

c) FIG. 2A shows a top view of a plate according to nail-plate combination of FIG. 1;

d) FIG. 2B shows a cross-sectional side view of the plate of FIG. 2A along cross-sectional line B-B;

h) FIG. 5A shows a perspective view of a blade screw of the nail-plate combination of FIG. 1A;

i) FIG. 5B shows a top view of the blade screw of FIG. 5A;

j) FIG. 5C shows a cross-sectional side view of the blade screw of FIGS. 5A and 5B taken along cross-section line D-D;

k) FIG. 6A shows a perspective view of inserting the nail into a bone according to an exemplary method of use of the nail-plate combination of FIG. 1A;

l) FIG. 6B shows a perspective view of inserting the blade into the bone and nail according to the exemplary method of FIG. 6A;

m) FIG. 6C shows a perspective view of the positioning the plate over the bone according to the exemplary method of FIG. 6A;

n) FIG. 6D shows a perspective view attaching the plate to the blade according to the exemplary method of FIG. 6A;

o) FIG. 6E shows a perspective view of attaching the plate to the bone according to the exemplary method of FIG. 6A;

p) FIG. 7A shows a perspective view of a nail-plate combination according to a second exemplary embodiment of the present invention;

q) FIG. 7B shows a cross-sectional side view of the nail-plate combination of FIG. 7A, taken along cross-sectional line D-D;

t) FIG. 9A shows a top view of a blade cap according to the nail-plate combination of FIG. 7A;

u) FIG. 9B shows across-sectional side view of the blade cap of FIG. 9A, taken along cross-sectional line F-F;

v) FIG. 10A shows a perspective view of positioning the plate on a head of a bone according to an exemplary method of use for nail-plate combination of FIG. 7A;

w) FIG. 10B shows a perspective view of attaching the plate to the bone according to the exemplary method of FIG. 10A;

x) FIG. 10C shows a perspective view of inserting the nail into the bone according to the exemplary method of FIG. 10B;

y) FIG. 10D shows a perspective view of inserting the blade into the bone and the nail according to the exemplary method of FIG. 10C;

z) FIG. 10E shows a perspective view of attaching the blade cap to the plate according to the exemplary method of FIG. 10A;

aa) FIG. 10F shows a perspective view of attaching a blade screw to the plate cap according to the exemplary method of FIG. 10A;

bb) FIG. 11A shows a perspective view of inserting the nail into the bone according to another exemplary method of use for the nail-plate combination of FIG. 7A;

cc) FIG. 11B shows a perspective view of inserting the blade into the bone and the nail according to the exemplary method of use of FIG. 11A;

dd) FIG. 11C shows a perspective view of placing the plate on the bone according to the exemplary method of use of FIG. 11A;

ee) FIG. 11D shows a perspective view of attaching the plate to the bone according to the exemplary method of use of FIG. 11A;

ff) FIG. 11E shows a perspective view of attaching the blade cap to the blade according to the exemplary method of use of FIG. 11A;

gg) FIG. 11F shows a perspective view of attaching the blade screw to the blade cap according to the exemplary method of use of FIG. 11E;

jj) FIG. 13A shows a top view of a plate according to the nail-plate combination of FIG. 12A;

kk) FIG. 13B shows a cross-sectional side view of the plate of FIG. 13A, taken along cross-sectional line G-G;

ll) FIG. 14 shows a side view of a nail according to the nail-plate combination of FIG. 13A;

nn) FIG. 15B shows a cross-sectional side view of the nail-plate combination of FIG. 15A, taken along cross-sectional line H-H;

ss) FIG. 17A shows a perspective view of inserting a nail into a bone according to an exemplary method of use for the nail-plate combination of FIG. 15A;

tt) FIG. 17B shows a perspective view of inserting a blade into the bone and the nail according to the exemplary method of FIG. 17A;

uu) FIG. 17C shows a perspective view of attaching the plate to the blade according to the exemplary method of FIG. 17A;

ww) FIG. 20 shows a perspective view of a plate according to a sixth exemplary embodiment of the present invention.

DETAILED DESCRIPTION

The present invention, which may be further understood with reference to the following description and the appended drawings, relates to systems and methods for providing fixation of bone fractures. Specifically, the present invention relates to nail and plate combinations that may be used to fix multipart fractures of one end of a bone. Exemplary embodiments of the present invention describe, for example, a combination comprising a plate and an intramedullary nail.

It should be noted that directional references used herein do not refer to particular frames of reference (e.g., the horizontal), but are employed merely to indicate directions relative to other parts of the devices described unless they specifically address direction relative to an external feature such as a bone. For example, the term top refers to a surface of a plate which, when placed on a bone in a desired orientation, faces away from the bone while a bottom refers to a surface facing the bone.

Figure 1A:
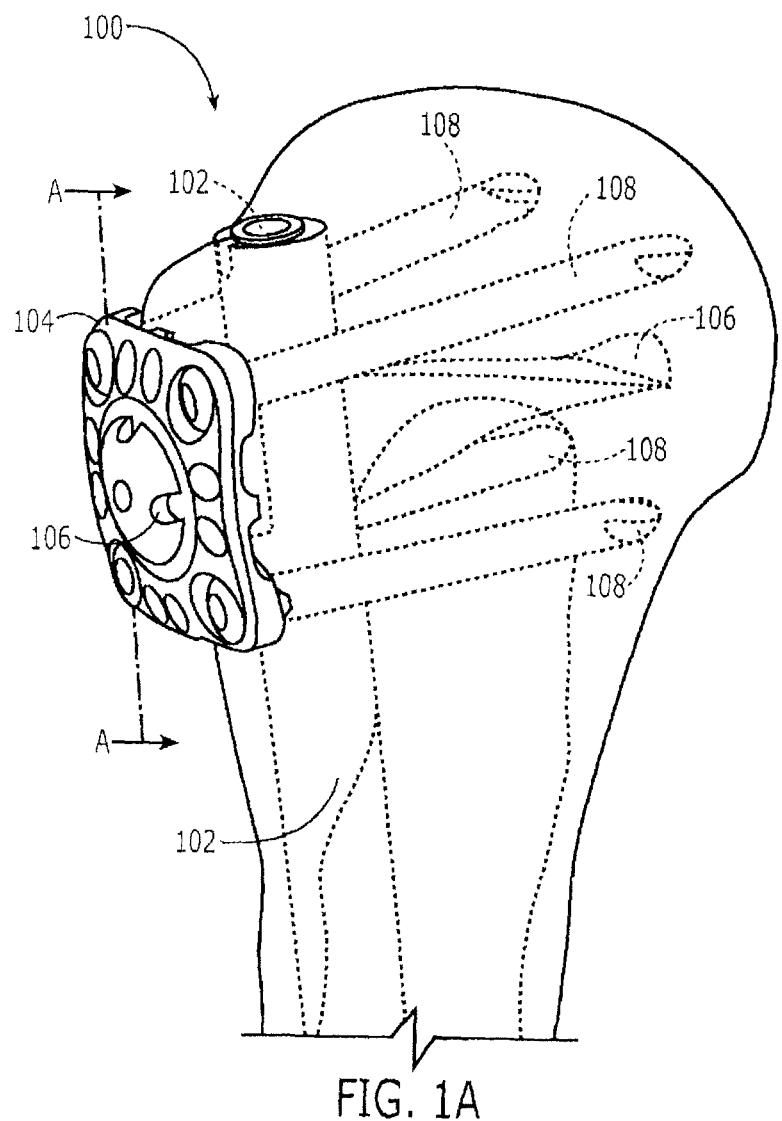
FIG. 1A shows a perspective view of a first exemplary embodiment of a nail-plate combination implanted in a bone.
Figure 1B:
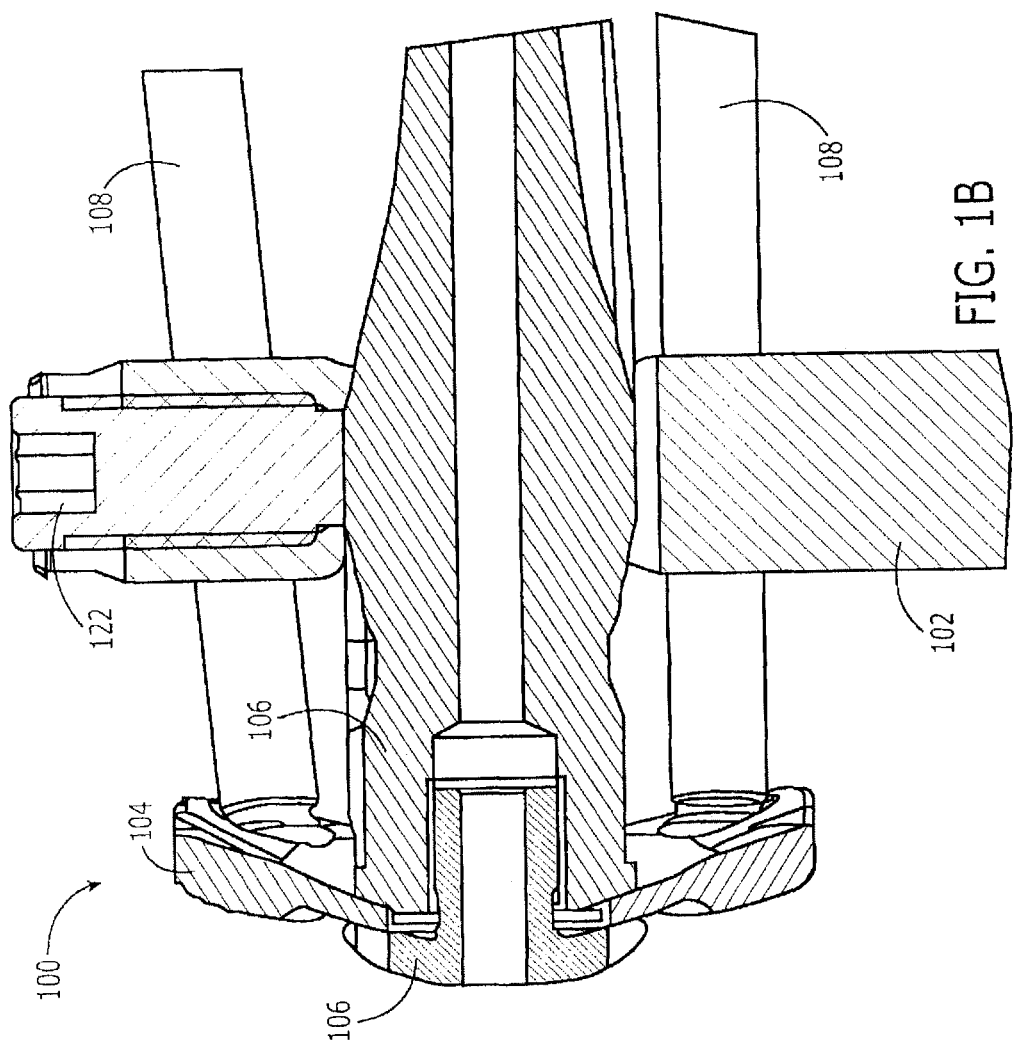
FIG. 1B shows a cross sectional view of the nail-plate combination of FIG. 1A, taken along cross-sectional line A-A.

As shown in FIGS. 1A and 1B, a nail-plate combination 100 according to a first exemplary embodiment of the present invention may comprise an intramedullary nail 102 and a plate 104, which may be connected to the intramedullary nail 102 via a connector 106. The nail-plate combination may further comprise fasteners 108 to fasten the plate 104 to an end of a bone 110 and an end cap 122 to lock the connector 106 within the intramedullary nail 102 and an end cap 122 to lock the connector 106 within the intramedullary nail 102.

Generally, the plate 104, as shown in FIGS. 2A and 2B, is sized and shaped to be disposed on a surface of an end of the bone 110. In an exemplary embodiment, the plate 104 may be square-shaped. The plate 104 preferably has a convex top surface 124 and a concave bottom surface 126 adapted to generally match the contour of the head of the bone 110 to which the plate 104 is to be affixed to minimize plate prominence and provide stable support thereto. The plate 104 further includes at least one connector opening 128, at least one fastener opening 130 and at least one suture opening 132 extending through the plate 104 from the top surface 124 to the bottom surface 126. In one embodiment, the connector opening 128 may be centrally located on the plate 104 and define an inner surface including threads 134. The fastener openings 130 and the suture openings 132 may be spaced around the connector opening 128 adjacent to a perimeter of the plate 104 and to a surface 129 immediately surrounding the connector opening 128.

The fastener openings 130 may be of any design known in the field for fixing plates to bones. For example, the fastener openings may define inner surfaces having threads 136 to accommodate the threaded heads of fasteners such as locking screws. Alternatively, the fastener openings 130 may be combi-holes as described in U.S. Pat. No. 5,709,686, U.S. Pat. No. 66,669,701 and U.S. Pat. No. 6,719,759, each of which is incorporated herein by reference in its entirety. A central axes of the fastener openings 130 may be disposed at angles relative to each other and/or to an axis of the connector opening 128 so that the fasteners pass therethrough into the bone 110 at desired angles relative to one another and to the connector 106 passed through the connector opening 128. For example, the fastener openings 130 may pass through the plate 104 with distal ends thereof angled to flare outward relative to one another and to the central axis of the connector opening 128 increasing the stability of the plate when it is attached to the bone 110. It will be understood by those of skill in the art that the although the plate 104 is shown as having six suture openings 132 and four fastener openings 130, any number of fastener and suture openings 130, 132 may be included in the plate 104.

The plate 104 may further comprise a guide opening 138 and a guide attachment opening 140. It will be understood by those of skill in the art that the guide opening 138 may be used to position a drill guide block relative to the plate 104 and the guide attachment opening 140 may be used to connect the plate 104 to a drill guide block. The guide attachment opening 140 may thus include threads 142 such that the drill guide block may be connected to the plate 104 by a threaded engagement.

Figure 3:
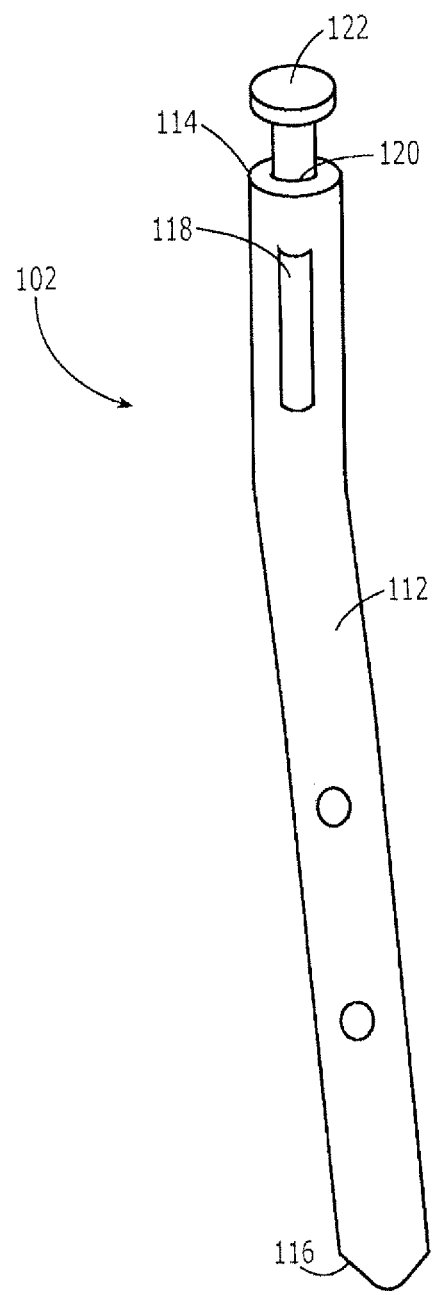
FIG. 3 shows a side view of a nail according to the nail-plate combination of FIG. 1A.

The intramedullary nail 102, as shown in FIG. 3, comprises a an elongate shaft 112 that may be slightly bent to follow a natural curvature of the medullary canal of the bone 110 into which it is inserted. The elongate shaft 112 extends from a driving end 114 to a non-driving end 116, which may be inserted into an opening in the bone 110 and driven distally into the medullary canal while the driving end 114 generally remains near the opening of the bone where it is accessible. Further, the nail 102 may include an oblong opening 118 extending through the shaft 112 near the driving end 114, an axial lumen 120 extending from an opening at the driving end 114 of the nail 102 along the longitudinal axis of the shaft 112 with an end cap 122 adapted to be secured in the opening at the driving end 114 of the axial lumen 120. Preferably, the oblong opening 118 extends diametrically from one side of the shaft to the other between diametrically opposed openings formed on the shaft 112 of the nail 102. In one embodiment, the opening 118 may be oblong, e.g., rectangular in cross-section with a length parallel to the axis of the shaft 112 greater than a width thereof perpendicular to the axis of the shaft 112. The axial lumen 120 extends from the driving end 114 through the opening. 118, toward a distal end of the shaft 112. The end cap 122 may, for example, be secured to the proximal end of the axial lumen 12 by threaded engagement such that the end cap 122 at least partially extends into the opening 118 and is securely fixed therein.

Figure 4B:
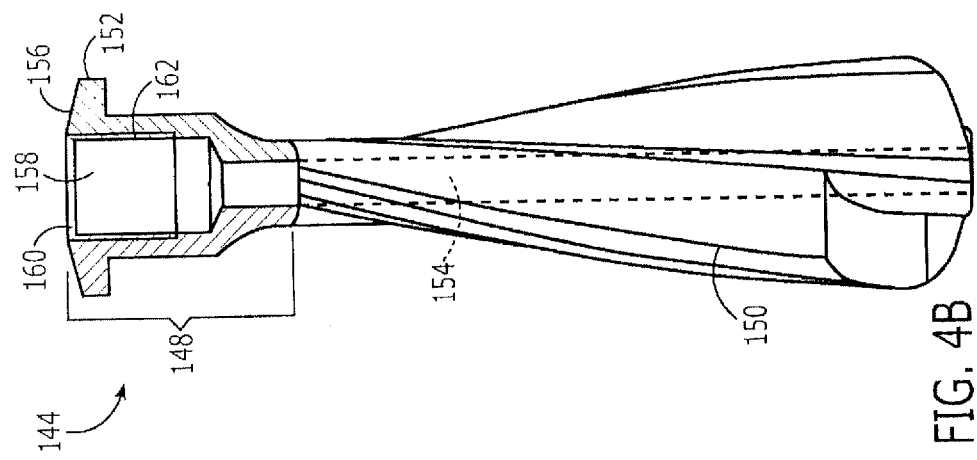
FIG. 4B shows a cross-sectional side view of the blade of FIG. 4A along cross-sectional line C-C.
Figure 4A:
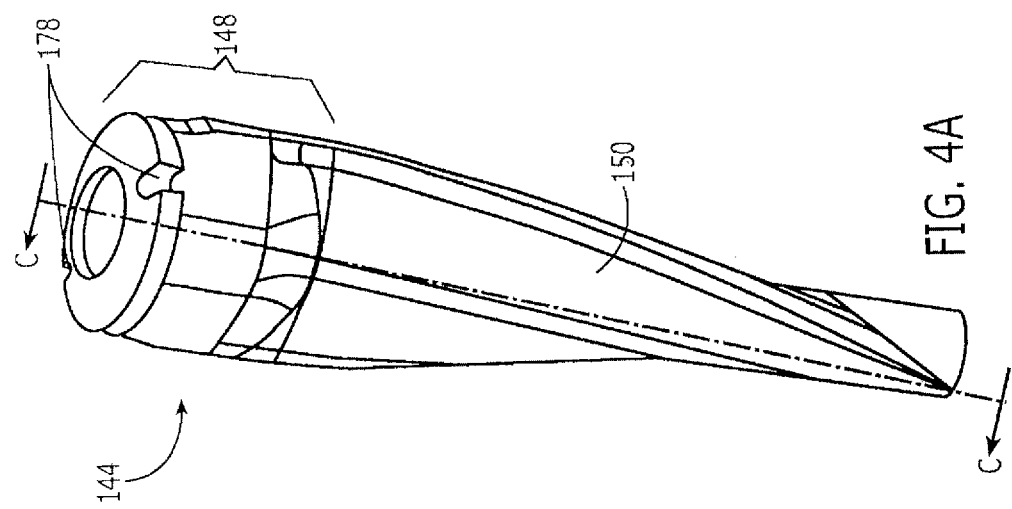
FIG. 4A shows a perspective view of a blade according to the nail-plate combination of FIG. 1A.

The plate 104 may be attached to the intramedullary nail 102 via the connector 106, which may be comprised of a spiral blade 144 and a blade screw 146. As shown in FIGS. 4A and 4B, the spiral blade 144 according to an exemplary embodiment of the present invention comprises a head portion 148, a body portion 150 extending from the head portion 148 and an annular flange 152 encircling a perimeter of a free end of the head portion 148. The head portion 148 and the body portion 150 are preferably integrally formed and extend along a common longitudinal axis. The body portion 150 forms a blade helically twisted about the longitudinal axis with a guidewire channel 154 extending the length of the spiral blade 150 in the longitudinal direction. As shown, the head portion 148 preferably has a generally circular shape with a top surface 156 having a generally rounded convex shape. Further, the head portion 148 has a screw recess 158 forming an opening 160 on the top surface 156 of the head portion 148 and extending longitudinally downward from the opening 160. The screw recess 158 defines an inner surface 162 having threads disposed thereon to mate with threads from other structures as described below. The annular flange 152 includes a driving means 178 which may be a pair of notched formed on opposite sides of the annular flange 152 such that a driving tool may be used for insertion of the blade screw 144. It will be understood by those of skill in the art, however, that other driving means may be included in the spiral blade 144 so long as a means is provided for the driving means to be inserted into the intramedullary nail 102 and the bone 110. Certain other aspects of the spiral blade 144 are described more fully in U.S. Pat. No. 6,409,730, which is incorporated herein by reference in its entirety. Although the nail-plate combination is described as including the spiral blade 144 to connect the plate 104 to the intramedullary nail 102, it will be understood by those of skill in the art that a variety of connection means may be used. For example, the connector 106 may include a blade that is straight rather than twisted in a spiral configuration.

As shown in FIGS. 5A-5C, a blade screw 146 according to an exemplary embodiment may include a head 164 and a shaft 166 extending downwardly therefrom. The head 164 and shaft 166 may be integrally formed and share a common longitudinal axis. The blade screw 146 has a guide wire channel 168 extending through the head 164 and the shaft 166 along the longitudinal axis. The head 164 may be rounded such that a top surface 170 is, for example, substantially convex while a bottom surface 172 is substantially concave. A circumference of the shaft 166 is sized to fit in the screw recess 158 of the spiral blade 144 and has threads 174 disposed on a surface thereof adapted to mate with the threads 162 in the screw recess 158 of the spiral blade 144. The shaft 166 may be inserted through the connector opening 128 and the head 164 may be sized and shaped to fit within the surface 129 of the plate 104, which surrounds the connector opening 128. Also, driving means 176 are disposed on the head 164 of the blade screw 146. As best shown in FIG. 9, the driving means 176 may include four notches cut out and evenly spaced around a perimeter of the head 164 of the blade screw 146 (e.g., a spanner-head type of screw draw). However, as would be understood by those skilled in the art, the driving means 176 may include any other types of grooves, recesses or projections adapted for engaging a driving tool (e.g., a flat-bladed, Philips, hex, or other type of screwdriver). Alternatively, the head 164 of the blade screw 146 may also a connection means for connecting the head 164 to the plate 104 such as, for example, threading that corresponds to the threading 134 of the connector opening 128 such that the head 164 attaches to the plate 104.

FIGS. 6A-6E show an exemplary method of use for the nail-plate combination 100. As shown in FIG. 6A, the intramedullary nail 102 is inserted into the intramedullary canal of the bone 110. The intramedullary nail 102 may be positioned therein using any known method in the art such as a guidewire 180. After the intramedullary nail 102 has been properly positioned, the spiral blade 144 may be driven into the bone 110 via driving means 178 such that the spiral blade 150 enters the opening 118 of the intramedullary nail 102, as shown in FIG. 6B. The spiral blade 144 may be aligned for insertion through the opening 118 of the nail 102 using any conventional method such as a guidewire 182. Once the spiral blade 144 is appropriately positioned, the end cap 122 of the intramedullary nail 102 may be secured within the axial lumen 120 of the driving end 114 such that the spiral blade 144 is securely positioned within the opening 118. As shown in FIG. 6C, the plate 104 may be positioned over the head portion 148 of the spiral blade 144 using the guidewire 182 such that the connector opening 128 aligns with the opening 160 of the spiral blade 144. After the plate 104 has been positioned, the shaft 166 of the blade screw 146 may then be inserted into the screw recess 158 of the spiral blade 144 until the lower surface 172 of the blade screw 146 abuts a top of the surface 129 of the plate 104 such that the threading 174 of the blade screw 146 engaged with the threading 162 of the spiral blade 144, as shown in FIG. 6D. Fasteners 108 may be inserted into the fastener openings 130 as shown in FIG. 6E to secure the plate 104 to the head of the bone 110.

As shown in FIGS. 7A and 7B, a nail-plate combination 100' according to a second exemplary embodiment of the present invention comprises an intramedullary nail 102' and a plate 104', which may be connected to the intramedullary nail 102' via a connector 106'. The nail-plate combination may further comprise fasteners 108' to fasten the plate 104' to an end of a bone 110' and an end cap 122' to lock the connector 106'. The nail-combination 100' may be substantially similar to the nail-combination 100 described above, but further comprises a blade cap 184' engaging the plate 104'. The intramedullary nail 102' and the connector 106' which include, for example, a spiral blade 144 and blade screw 146, are substantially the same as in the nail-plate combination 100.

Figure 8B:
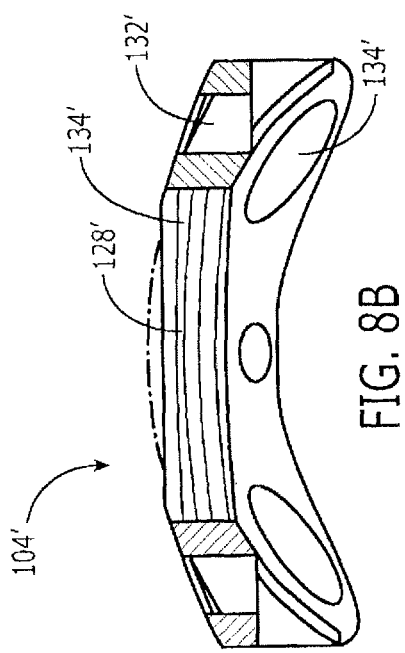
FIG. 8B shows a cross-sectional side view of the plate of FIG. 8A, taken along cross-sectional line E-E.
Figure 8A:
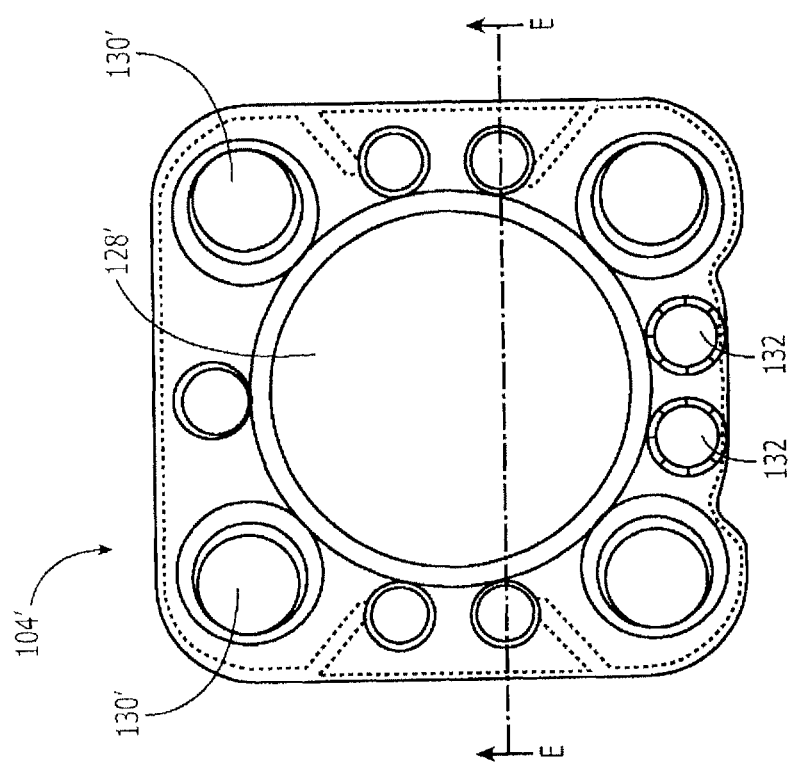
FIG. 8A shows a top view of a plate according to the nail-plate combination of FIG. 7A.

As shown in FIGS. 8A and 8B, the plate 104' may be substantially similar to the plate 104 as described above. The plate 104 may be substantially square with rounded corners and at least one connector opening 128' along with fastener openings 130' and suture openings 132' spaced around the connector opening 128' adjacent to a perimeter of the plate 104'. A diameter of a connector opening 128' may, however, be larger than the connector opening 128 of the plate 104, such that the connector opening 128' may accommodate the blade cap 184'. The connector opening 128' may include threads 134' along an inner surface thereof. The fastener openings 120' and suture openings 132' may be substantially similar to the fastener and suture openings 130, 132 of the plate 104.

As shown in FIGS. 9A and 9B, the blade cap 184' may be substantially disc-shaped with a top surface 186' that is rounded and convex and a bottom surface 188' that is rounded and concave. The blade cap 184' is sized and shaped to fit within the connector opening 128' of the plate 104'. In a preferred embodiment, the blade cap 184' includes threads 190' disposed on a circumferential surface of the blade cap 184' to engage the threads 134' of the connector opening 128'. The blade cap 184' includes a central opening 192' extending, for example, along a central axis of the blade cap 184' from the top surface 186' to the bottom surface 188'. Further, the blade cap 184' may include a driving feature 194' disposed on the top surface 186'. The driving feature 194' may include, for example, four circular recesses evenly spaced around the central opening 192' and adapted to receive a spanner-head type of screw driver. It will be understood by those of skill in the art, however, that the driving means 194' may take a variety of forms so long as the driving feature 194' may be used to drive the blade cap 184' into position within the connector opening 128' of plate 104'. For example, the driving feature 194' may be other types of grooves or recesses adapted for use with a flat-bladed, Phillips, hex or other types of screwdrivers.

FIGS. 10A-10F show an exemplary method of use for the nail-plate combination 100'. As shown in FIG. 10A, the plate 104' may be positioned on a head of the bone 110' using any known positioning means, such as a guidewire 182'. The plate 104' may be fixed to the bone 110' using fasteners 108', as shown in FIG. 10B. As shown in FIG. 10C, once the plate 104 has been secured to the bone 110, the intramedullary nail 102 may be inserted into the medullary canal of the bone 110 using any known positioning means, such as a guidewire 180'. The spiral blade 144' may then be inserted through the connector opening 128' of the plate 104' and advanced therethrough such that an elongated shaft 150' of the spiral blade 144' are received within an opening 118 of the intramedullary nail 102, as shown in FIG. 10D. It will be understood by those of skill in the art that the spiral blade 144' may be advanced via any known driving mechanism. The spiral blade 144 may be secured therewithin by inserting the end cap 122' into a proximal opening 120' of the intramedullary nail 102'. As shown in FIG. 10E, the blade cap 184' may then be driven into the connector opening 128' with the threading 190' of the blade cap 184' engaging the threading 134' of the connector opening 128'. Once the blade cap 184' is positioned within the connector opening 128', a shaft of the blade screw 146' may be inserted into a screw recess of the spiral blade 144' until a head of the blade screw 146' abuts the top surface 186' of the blade cap 184', as shown in FIG. 10F, such that the blade screw 146' and the spiral blade 144' engage one another, connecting the plate 104' to the intramedullary nail 102'.

It will be understood by those of skill in the art that the exemplary method described above in reference to nail-plate combination 100' may similarly be used for nail-plate combination 100 by positioning the plate 104 on the head of the bone 110 prior to inserting the intramedullary nail 102 into the medullary canal of the bone. Likewise, the nail-plate combination 100' may be used similarly to the method described above in reference to the nail-plate combination 100 in which the intramedullary nail 102 is inserted into the bone 110 prior to positioning of the plate 104.

For example, 11A-11F show another exemplary method of use for the nail-plate combination 100'. As shown in FIG. 11A, the intramedullary nail 102' is inserted into the intramedullary canal of the bone 110'. The intramedullary nail 102' may be positioned therein using any known method such as the guidewire 180'. After the intramedullary nail 102' has been properly positioned, the spiral blade 144' may be driven into the bone 110' via any known driving mechanism such that the spiral body 150' enters the opening 118' of the intramedullary nail 102', as shown in FIG. 11B. The spiral blade 144' may be aligned for insertion through the opening 118 of the nail 102' using any conventional method such as the guidewire 182'. Once the spiral blade 144' has been appropriately positioned, the end cap 122' of the intramedullary nail 102' may be secured within an axial lumen such that the spiral blade 144' is securely positioned within the opening 118. As shown in FIG. 11C, the plate 104' may then be positioned over a head portion of the spiral blade 144' using the guidewire 182' such that the connector opening 128' aligns with an opening of a screw recess of the spiral blade 144'. After the plate 104' has been positioned, fasteners 108' may be inserted into the fastener openings 130', as shown in FIG. 11D, to secure the plate 104' to the head of the bone 110'. Once the plate 104' has been secured to the bone 110', the blade cap 184' may be positioned within the connector opening 128', as shown in FIG. 11E, and driven therethrough so that threading 190' of the blade cap 184' engages threading 134' of the connector opening 128. A shaft 166' of the blade screw 146' may then be inserted into the central opening 192' of the blade cap 184' to engage with the screw recess 158' of the spiral blade 144', as shown in FIG. 11F. The blade screw 146' may be driven until a lower surface of a head portion of the blade screw 146' abuts the top surface 186' of the blade cap 184'. Engagement of the blade screw 146' with the 144' fixes the intramedullary nail 102' and the plate 104' relative to one another.

Figure 12A:
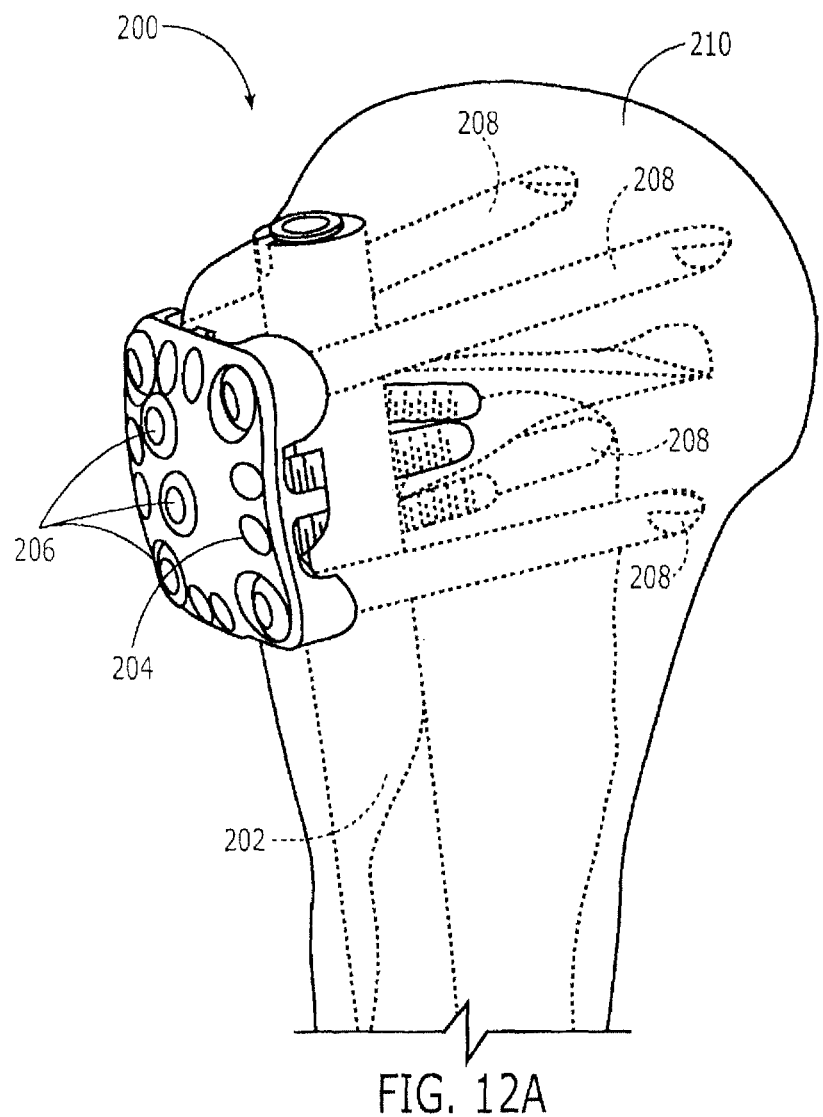
FIG. 12A shows a perspective view of a nail-plate combination according to a third exemplary embodiment of the present invention.
Figure 12B:
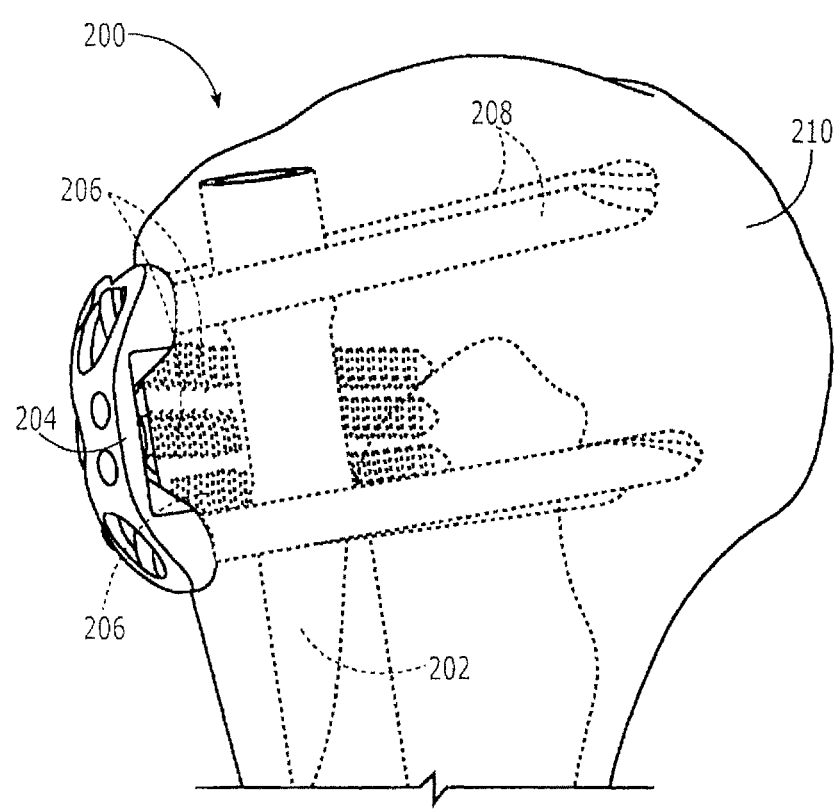
FIG. 12B shows a side view of the nail-plate combination of FIG. 12A.

As shown in FIGS. 12A and 12B, a nail-plate combination 200, according to another exemplary embodiment of the present invention comprises an intramedullary nail 202 and a plate 204, which may be connected via at least one connector 206. The nail-plate combination 200 may further comprise at least one fastener 208 to securely attach the plate 204 to a bone 210. The nail-plate combination 200 may be substantially similar to the nail-plate combination 100, except that the plate 204 includes at least one connector opening 228 that is adapted to receive and secure the connector 206, which may be a screw.

As shown in FIGS. 13A and 13B, the plate 204 may be substantially square with at least one connector openings 228 in a central portion thereof. Although the plate 204 is shown as including three connector openings 228, it will be understood by those of skill in the art that a variety of numbers of connector openings 228 may be included. Each connector opening 228 may be formed substantially along an axis X of the plate 204 such that the connectors 206 may enter an opening 218 of the intramedullary nail 202 when the connector 206 is inserted through the connector opening 228. The connector opening 228 may be oriented so that they flare outward away from one another in a distal direction. For example, if a central axis of a central-most one of the connector openings 228 extends substantially perpendicular to the plate 204, the axes of the connector openings 228 above and below this central-most opening 228 will angle away from one another distally so that connectors inserted therethrough will pass into the bone with a distance between distal ends thereof greater than a distance between the respectively connector openings 228. Each connector opening may include threading 234 such that the opening may engage the connector 206.

The plate 204 may also include fastener openings 230, suture openings 232, a guide opening 238 and a guide attachment opening (not shown) similarly to the plate 104. The fastener openings 230, suture opening 232 and guide opening 238 may be similar to those of the plate 100. For example, the fastener openings 230 may define inner surfaces having threads to accommodate threaded heads of fastener screws. Alternatively, the fastener openings 230 may be combi-holes as described in U.S. Pat. No. 5,709,686, U.S. Pat. No. 66,669,701 and U.S. Pat. No. 6,719,759, each of which is incorporated herein by reference in its entirety. A central axes of the fastener openings 230 may be disposed at angles relative to each other and/or to an axis of the connector opening 228 so that the fasteners pass therethrough into the bone 210 at desired angles relative to one another and to the connector 206 passed through the connector opening 228.

As shown in FIG. 14, the connector 206 may be a screw including a head portion 248 and an elongated body portion 250. The connector 206 may also include a threading 254 extending along a length of the connector 206 such that the threading 254 along the body portion 250 may engage the opening 218 and be secured in place by an end cap 122 of the intramedullary nail 202, while the threading 254 along the head portion 248 may engage the threading 234 of the connector opening 228 such that the connectors 206 are secured in place.

The nail-plate combination 200 may be used in the same manner as described above in regard to the nail-plate combination 100. Specifically, the nail-plate combination 200 may be used by positioning the plate 204 over an end of the bone 210 prior to insertion of the intramedullary nail 202 within the intramedullary canal of the bone 210. Particularly, the plate 204 may be positioned over the head portion of the bone 210 using a guidewire or other positioning means. Once a desired position of the plate 204 has been attained, fasteners 208 may be inserted into the fastener openings 230 so that the plate 204 is secured in place. Once the plate 204 has been secured on the bone 210, the intramedullary nail 202 may be inserted into the intramedullary canal of the bone 210 using a guidewire or other positioning means. Once the intramedullary nail 202 has been inserted therein, each connector 206 may be inserted into the connector opening 228 and through the opening 218 of the intramedullary nail 202 until the head portion 248 of the connector 206 engages the threading 234 of the connector opening 228. The end cap 222 may then be inserted into a proximal opening 220 of the intramedullary nail 202 such that the connectors 206 are held in place within the opening 218.

Figure 15A:
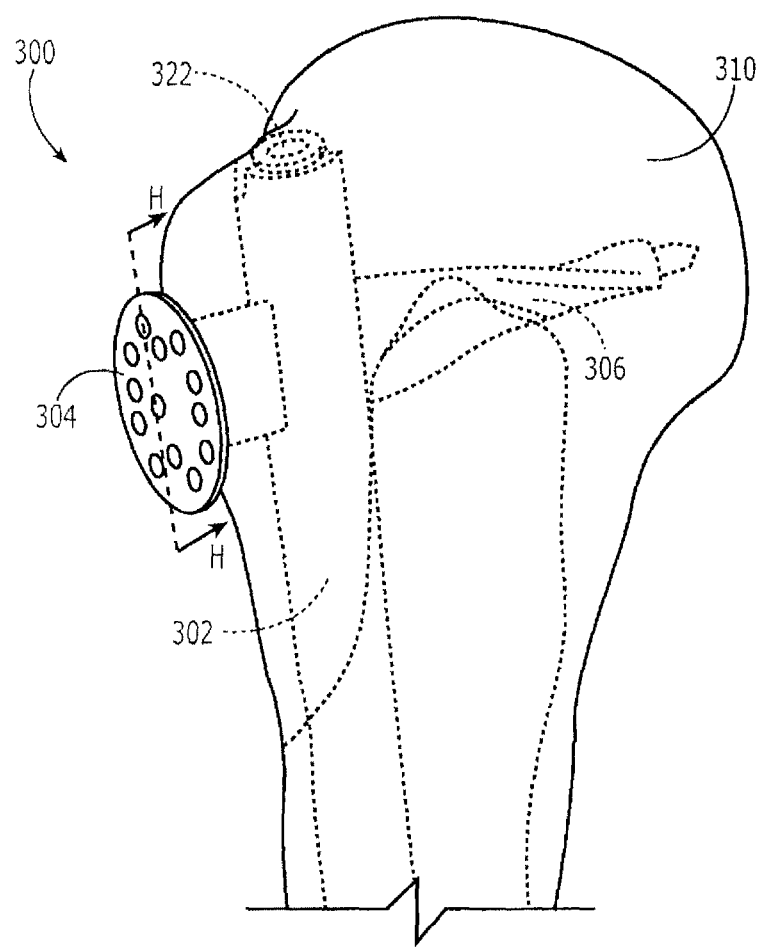
FIG. 15A shows a perspective view of a nail plate combination according to a fourth exemplary embodiment of the present invention.
Figure 16A:
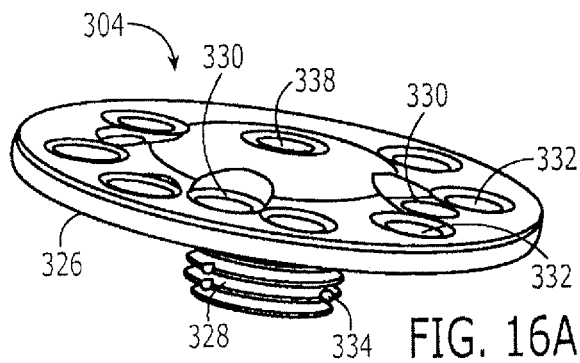
FIG. 16A shows a perspective view of a plate according to the nail-plate combination of FIG. 15A.
Figure 16B:
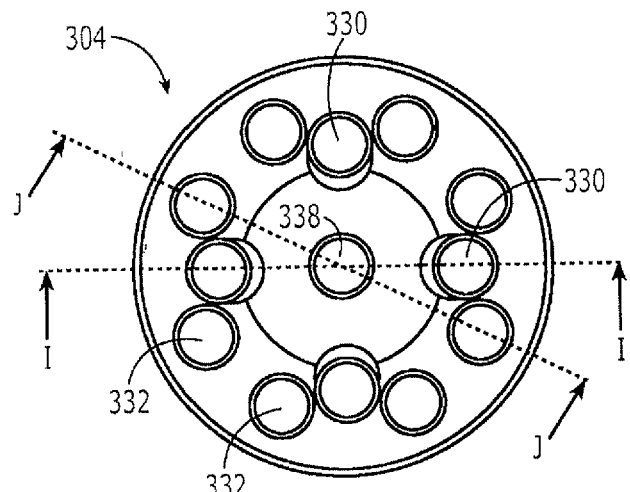
FIG. 16B shows a top view of a nail-plate combination of FIG. 16A.
Figure 16C:
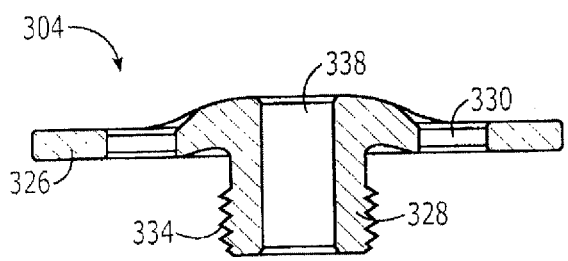
FIG. 16C shows a cross-sectional side view of the plate of FIG. 16A, taken along cross-sectional line I-I.
Figure 16D:
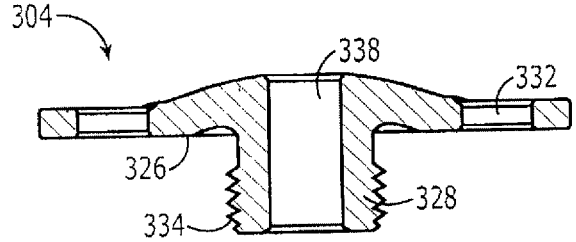
FIG. 16D shows a cross-sectional side view of the plate of FIG. 16A, taken along cross-sectional line J-J.

As shown in FIGS. 15A and 15B, a nail-plate combination 300 according to another exemplary embodiment of the present invention comprises an intramedullary nail 302, a plate 304 and a connector 306. The nail-plate combination 300 may be substantially similar to the nail-plate combination 100 as described above, except that the plate 304, shown in FIGS. 16A-16D, includes a protrusion 328 extending from a bottom surface 326 thereof, instead of a connector opening. The protrusion 328 may include threading 334 such that the protrusion 328 may mate with the connector 306, a spiral blade substantially similar to the spiral blade 144. The spiral blade connector 306 includes a recess 358 at a distal end thereof with proximal threading 362 for engaging the threading 334 of the protrusion 328. Additionally, the plate 304 may be substantially circular with fastener openings 330 and suture openings 332 distributed about a guide channel 338 located centrally thereof.

The nail-plate combination 300 may be used according to a method substantially similar to the technique described in regard to the nail-plate combination 100, as shown in FIGS. 17A-17C. Similarly to the nail-plate combination 100, a nail 302 is inserted into a medullary canal of a bone 310, as shown in FIG. 17A. The nail 302 may be positioned using any known method such as for example, a guidewire 380. Once the nail 302 is positioned within the bone 310, a connector 306 may be inserted into an opening of the nail 302, as shown in FIG. 17B. The connector may be inserted into the bone via the opening of the nail 302 using any known method such as, for example, a guidewire 382. However, instead of using a blade screw and a separate plate, as described in regard to nail-plate combination 100, the plate 304 may be positioned over a head of the spiral blade connector 306 once it has been inserted through an oblong bore (not shown) of the intramedullary nail 302, as shown in FIG. 17C. The protrusion 328 of the plate 304 engages the spiral blade connector 306. Additionally, as described above, fasteners may be inserted through the fastener holes 330 and sutures may be made via suture openings 332 to further secure the plate 304 in the appropriate position.

Figure 18:
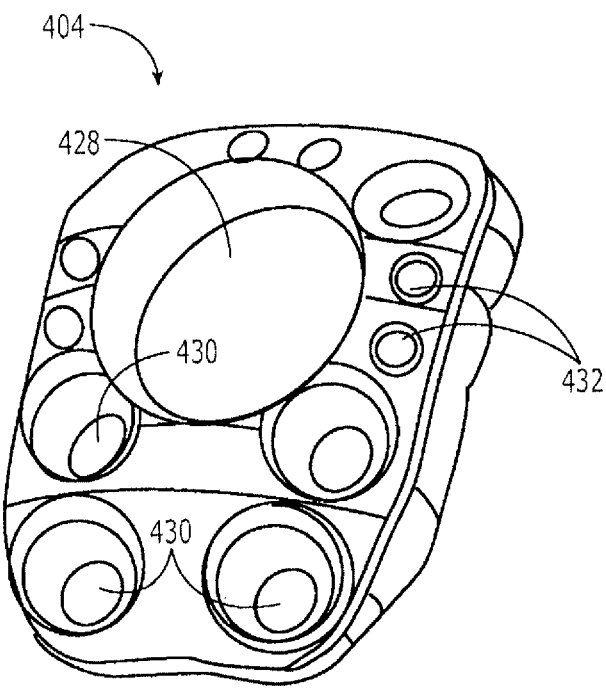
FIG. 18 shows a perspective view of a plate according to a fourth exemplary embodiment of the present invention.

FIG. 18 shows a plate 404 according to another embodiment of the present invention. It will be understood by those of skill in the art that the plate 404 may be used in place of either plate 104, 104' or 204 as described above in the nail-plate combinations 100, 200. The plate 404 may have a substantially rectangular shape, a centrally located connector opening 428, and a plurality of fastener openings 430 and suture openings 432 formed therethrough. For each of two corners of the plate 404 the plate 404 may include a single fastener opening formed therethrough while the other two corners of the plate 404 may each have two fastener openings 430 formed therethrough. The fastener openings 430 and the suture openings 432 may be substantially similar to the fastener and suture openings 130, 132 described above in regard to nail-plate combination 100. The connector opening 428 may be substantially similar to either of the connector openings 128 or 228 as described above in regard to nail plate combination 100 and nail plate combination 200, respectively. For example, the connector opening 428 may be adapted to receive either a spiral blade 144 and a blade screw 146 or may be adapted to receive at least one screw connector 206. It will be understood by those of skill in the art that the plate 404 may have any number of fastener openings 430 and suture openings 432.

Figure 19:
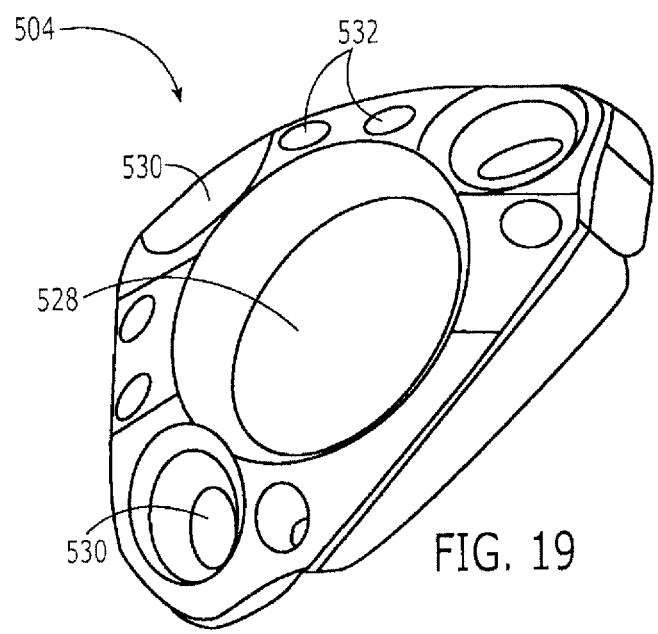
FIG. 19 shows a perspective view of a plate according to a fifth exemplary embodiment of the present invention; and xx)

FIG. 19 shows a plate 504 according to another embodiment of the present invention, which will be understood by those of skill in the art as capable of being used in place of either plates 104, 104' or 204 of the nail-plate combinations 100, 100', 200 described above. The plate 504 may be substantially similar to the plate 404 described above, except that plate 504 has a substantially triangular shape. Similarly, the plate 504 may include a centrally located connector opening 528, a plurality of fastener openings 530 and a plurality of suture openings 532 spaced around the perimeter of the plate 504.

FIG. 20 shows a plate 604 according to another embodiment of the present invention, which will be understood by those of skill in the art as capable of being used in place of plate 104, 104', 204 in the nail-plate combinations 100, 100', 200. The plate 604 may be substantially similar to the plate 104, but may additionally include an outrigger arm 684. A substantially square portion of the plate includes a connector opening 628, fastener openings 630 and suture openings 632 while the outrigger arm 684 extends from the square portion and includes at least one opening 686 therethrough. The connector opening 628 may be adapted to receive either of the connectors 106, 206 described above. The outrigger arm 684 may move relative to the square portion by. For example, the outrigger arm 684 may be rotatable relative to the square portion. The outrigger arm 684 may be used to fix a lesser tuberosity of the humeral head.

It will be understood by those of skill in the art that although the plates according to the exemplary embodiments of the present invention are described as being of a particular shape (e.g., square, rectangular, triangular), the plates may be of a variety of shapes so long as they are able to function as described above. For example, the plates described above may also be substantially round or oval-shaped.

It will be apparent to those skilled in the art that various modifications and variations may be made to the structure and methodology of the present invention without departing from the spirit and scope thereof. This description illustrates specific examples and is not intended to limit the scope of the invention of which it is to be bound. Thus, it is intended that the present invention cover the modifications and the variations of this invention provided that they come within the scope of the appended claims and their equivalents.

What is claimed is:

1. A device for treating a bone, comprising:
    a plate having a connector opening and a first fastener receiving lumen extending therethrough, the first fastener receiving lumen being sized and shaped to receive therethrough a bone fastener, the plate further having a recessed portion surrounding the connector opening;
    a nail sized and shaped for insertion in a medullary canal of a target bone, the nail including an elongate shaft and an opening extending through the shaft; and
    a connector sized and shaped so that, when the plate is positioned over a target portion of bone in a desired alignment with the nail, the connector may be passed into the target portion of bone via the connector opening and into the opening of the nail, the shape of the connector mechanically engaging and interlocking with the opening to form an angularly stable connection between the plate and the nail, the shape of the connector configured to fit within the recessed portion.

2. The device of claim 1, wherein the plate has a substantially concave bone-facing surface generally matching a contour of the target portion of bone.

3. The device of claim 1, wherein an inner surface of the connector opening is threaded.

4. The device of claim 3, wherein the connector includes one of a spiral blade and a straight blade.

5. The device of claim 4, further comprising a threaded blade cap including a threaded outer surface sized to threadedly engage the connector opening.

6. The device of claim 1, wherein the connector includes a bone screw, a portion of which is adapted to mate with threads of the first fastener receiving lumen.

7. The device of claim 1, wherein the plate includes a suture opening extending therethrough from a bone-facing surface thereof to an outer surface opposite the bone-facing surface.

8. The device of claim 1, wherein the plate is substantially square.

9. The device of claim 1, wherein the plate is substantially rectangular.

10. The device of claim 1, wherein the plate is substantially triangular.

11. A device for treating a bone, comprising:
a plate having a connector opening and a first fastener receiving lumen extending therethrough, the first fastener receiving lumen being sized and shaped to receive therethrough a bone fastener;
a nail sized and shaped for insertion in a medullary canal of a target bone, the nail including an elongate shaft and an opening extending through the shaft; and
a connector sized and shaped so that, when the plate is positioned over a target portion of bone in a desired alignment with the nail, the connector may be passed into the target portion of bone via the connector opening and into the opening of the nail, the shape of the connector engaging the opening to form an angularly stable connection between the plate and the nail, wherein the connector opening includes at least one locking element receiving location and the connector includes a corresponding at least one elongate locking element that is insertable, when the plate is positioned over the target portion of bone in the desired alignment with the nail, into the opening via a respective one of the locking element receiving locations.

12. The device of claim 11, wherein the at least one locking element receiving location comprises discrete holes extending through the plate separate from one another.

13. The device of claim 11, wherein the at least one locking element receiving location defines a central axis substantially along which a locking element inserted therethrough will pass into the opening, the central axes of the locking element receiving locations being angled relative to one another so that locking elements inserted therethrough into the slot will flare outward relative to one another to non-rotatably engage the slot.

14. The device of claim 11, wherein the locking element is a single connector connecting the plate and the nail.

15. A method of treating a bone, comprising the steps of:
securing to a target portion of a bone to be treated a plate including a connector opening and a fastener opening extending therethrough, the plate further having a recessed portion surrounding the connector opening;
inserting a fastener through the fastener opening;
inserting into a medullary canal of the bone a nail including an elongate shaft and an opening extending through the shaft transverse to a longitudinal axis of the shaft;
inserting a connector through the target portion of the bone via the connector opening and into the opening of the nail, at least a portion of the connector being shaped to mechanically engage and interlock with the opening of the nail so that the connector is non-rotatable therein; and
connecting the connector to the connector opening, a further portion of the connector configured to fit within the recessed portion.

16. The method of claim 15, wherein the connector includes one of a spiral blade and a straight blade.

17. The method of claim 15, further comprising coupling the connector to the plate to non-rotatably couple the plate and the nail.

18. A device for treating a bone, comprising:
a plate having a connector opening and a first fastener receiving lumen extending therethrough, the first fastener receiving lumen being sized and shaped to receive therethrough a bone fastener;
a nail sized and shaped for insertion in a medullary canal of a target bone, the nail including an elongate shaft and an opening extending through the shaft; and
a connector sized and shaped so that, when the plate is positioned over a target portion of bone in a desired alignment with the nail, the connector may be passed into the target portion of bone via the connector opening and into the opening of the nail, the shape of the connector engaging the opening to form an angularly stable connection between the plate and the nail, wherein an inner surface of the connector opening is threaded, wherein the connector includes one of a spiral blade and a straight blade, and wherein the spiral blade includes a blade screw opening and wherein the device further comprises a blade screw sized for insertion through the blade cap into the blade screw opening to secure the spiral blade to the plate.

19. A device for treating a bone, comprising:
a plate having a connector opening and a first fastener receiving lumen extending therethrough, the first fastener receiving lumen being sized and shaped to receive therethrough a bone fastener;
a nail sized and shaped for insertion in a medullary canal of a target bone, the nail including an elongate shaft and an opening extending through the shaft; and
a connector sized and shaped so that, when the plate is positioned over a target portion of bone in a desired alignment with the nail, the connector may be passed into the target portion of bone via the connector opening and into the opening of the nail, the shape of the connector engaging the opening to form an angularly stable connection between the plate and the nail, wherein an inner surface of the connector opening is threaded, wherein the connector includes one of a spiral blade and a straight blade, and further comprising a second fastener receiving lumen, central axes of the first and second fastener receiving lumens being aligned relative to one another so that fasteners inserted therethrough into the bone diverge from one another as they move into the bone.

20. A method of treating a bone, comprising the steps of:
securing to a target portion of a bone to be treated a plate including a connector opening and a fastener opening extending therethrough, inserting a fastener through the fastener opening;
inserting into a medullary canal of the bone a nail including an elongate shaft and an opening extending through the shaft transverse to a longitudinal axis of the shaft; and
inserting a connector through the target portion of the bone via the connector opening and into the opening of the nail, at least a portion of the connector being shaped so that, when received within the opening of the nail, the connector is non-rotatable therein, wherein the connector opening includes at least one locking element receiving location and the connector includes a corresponding at least one elongate locking element that is insertable, when the plate is positioned over the target portion of bone in a desired alignment with the nail, into the nail opening via a respective one of the locking element receiving locations.

21. A device for treating a bone, comprising:

a nail sized and shaped for insertion in a medullary canal of a target bone, the nail including an elongate shaft and an opening extending through the;

a connector insertable through a slot, a portion of the connector sized and shaped to mechanically engage and interlock with the nail opening so that the connector is non-rotatable therewithin; and a plate having a protrusion extending from a distal surface of the plate and a first fastener receiving lumen extending therethrough, the protrusion being engageable with a proximal end of the connector, the first fastener receiving lumen being sized and shaped to receive therethrough a bone fastener, the connector being connectable to the plate.

\* \* \* \* \*